United States Patent [19]

Kalnes

[11] Patent Number: 5,780,695
[45] Date of Patent: *Jul. 14, 1998

[54] PROCESS FOR THE SELECTIVE SATURATION OF OLEFIN-CONTAINING HALOGENATED ORGANIC STREAMS

[75] Inventor: Tom N. Kalnes, Des Plaines, Ill.

[73] Assignee: UOP, Des Plaines, Ill.

[*] Notice: The term of this patent shall not extend beyond the expiration date of Pat. No. 5,637,782.

[21] Appl. No.: 741,810

[22] Filed: Oct. 31, 1995

Related U.S. Application Data

[63] Continuation-in-part of Ser. No. 348,416, Dec. 2, 1994, Pat. No. 5,637,782.

[51] Int. Cl.$^6$ .............................. C07C 17/38; C07C 19/08
[52] U.S. Cl. ...................... 570/262; 570/101; 570/177; 570/175
[58] Field of Search .................. 570/262, 101, 570/177, 175

[56] References Cited

U.S. PATENT DOCUMENTS

| | | |
|---|---|---|
| 2,550,953 | 5/1951 | Barrick . |
| 4,145,367 | 3/1979 | Boozalis et al. . |
| 4,923,590 | 5/1990 | Kalnes et al. . |
| 4,929,781 | 5/1990 | James, Jr. et al. . |

*Primary Examiner*—Alan Siegel
*Attorney, Agent, or Firm*—Thomas K. McBride; John G. Tolomei; John G. Cutts, Jr.

[57] ABSTRACT

A process for saturating an olefin-containing halogenated organic stream to produce saturated halogenated organic compounds while minimizing the hydrodehalogenation of the organic compounds.

8 Claims, 1 Drawing Sheet

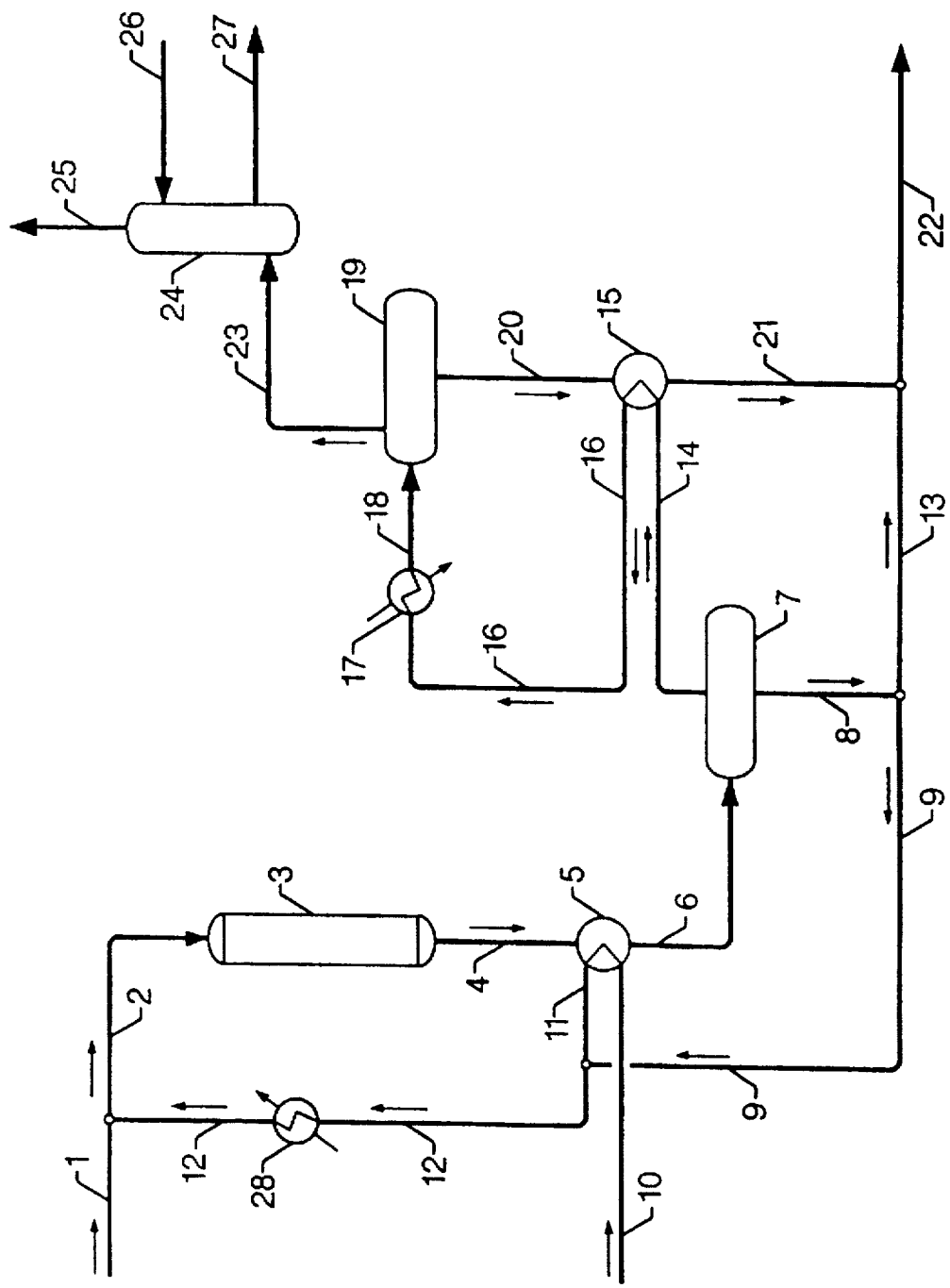

PROCESS FOR THE SELECTIVE SATURATION OF OLEFIN-CONTAINING HALOGENATED ORGANIC STREAMS

CROSS-REFERENCE TO RELATED APPLICATION

This application is a continuation-in-part of application Ser. No. 08/348,416 filed on Dec. 2, 1994, now U.S. Pat. No. 5,637,782.

BACKGROUND OF THE INVENTION

The field of art to which this invention pertains is the selective saturation of olefin-containing halogenated organic compounds while minimizing the hydrodehalogenation of the organic compounds and the resulting potential production of halide-free hydrocarbon compounds.

There is a steadily increasing demand for technology which is capable of treating or converting olefin-containing halogenated organic compounds to produce saturated halogenated organic compounds with essentially no formation of hydrogen halide compounds.

With the increased environmental emphasis for the treatment and recycle of organic streams including by-product and waste streams containing halogenated compounds, there is an increased need for improved processes to selectively convert certain organic streams. For example, during the disposal or recycle of potentially environmentally harmful organic waste streams, an important step in the total solution to the problem is to chemically transform a potentially hazardous organic waste stream to a useful product stream which may subsequently be handled in an environmentally acceptable manner. One environmentally attractive method of treating halogenated organic waste streams is by hydrogenation. Often in an industrial complex used to process or produce petrochemicals and organic compounds, there are by-product or waste streams which must be treated, converted, recycled or otherwise managed. Therefore, those skilled in the art have sought to find feasible and economical techniques to convert organic waste streams containing halide compounds to hydrogenated organic compounds.

INFORMATION DISCLOSURE

In U.S. Pat. No. 4,145,367 (Boozalis et al), a process is disclosed for removing chlorinated hydrocarbon impurities from 1,2-dichloroethane streams by partially or completely hydrogenating some or all of the impurities therein by passing hydrogen into the feed stream in the presence of a palladium hydrogenation catalyst under conditions which do not promote the decomposition of the dichloroethane.

In U.S. Pat. No. 4,929,781 (James, Jr. et al), a process is disclosed for the simultaneous hydroconversion of a first feedstock comprising unsaturated, halogenated organic compounds and a second feedstock comprising saturated, halogenated organic compounds. Hydrogen halide is recovered with a lean aqueous solution.

In U.S. Pat. No. 4,923,590 (Kalnes et al), a process is disclosed for treating a temperature-sensitive hydrocarbonaceous stream containing a non-distillable component to produce a hydrogenated distillable hydrocarbonaceous product and a heavy product containing the non-distillable component while minimizing thermal degradation of the hydrocarbonaceous stream. The '590 patent teaches that a hydrogen-rich gaseous stream may be recycled. One purpose of the hydrogen-rich gaseous stream having a temperature greater than the feed stream is to vaporize at least a portion of the feed which is then introduced into the hydrogenation reaction zone and another purpose is to supply hydrogen for the hydrogenation reaction. In one embodiment, the '590 patent teaches that when the feed to the hydrogenation zone comprises halogenated compounds, the aqueous scrubbing solution preferably contains a basic compound to neutralize the acid. The process of the '590 patent hydrodehalogenates organic compounds to produce hydrogen halide compounds and hydrogenated distillable hydrocarbonaceous compounds.

In U.S. Pat. No. 2,550,953 (Barrick), a process is disclosed for obtaining a short chain fluoroalkane which comprises heating an unsaturated acyclic fluorohydrocarbon containing from 2 to 9 carbon atoms with hydrogen in the liquid phase in the presence of a hydrogenation catalyst.

BRIEF SUMMARY OF THE INVENTION

The invention provides a process for selectively saturating an olefin-containing halogenated organic stream to produce saturated halogenated organic compounds while minimizing the hydrodehalogenation of the organic compounds. The olefin-containing halogenated organic stream is contacted with hydrogen and a liquid recycle stream comprising saturated halogenated compounds, and the resulting admixture is contacted with a hydrogenation catalyst in a hydrogenation reaction zone at selective hydrogenation conditions. The resulting effluent from the hydrogenation reaction zone is cooled to produce a saturated liquid halogenated organic stream and a vapor stream containing hydrogen, normally gaseous hydrocarbons, saturated halogenated organic compounds and hydrogen halide. At least a portion of the liquid saturated halogenated organic stream is recycled to the fresh feed stream to attain the required reaction temperature and to act as a diluent and heat sink in the hydrogenation reaction zone. In a preferred embodiment, the recycle liquid contains dissolved hydrogen and is heated or cooled as required to control the reaction zone inlet temperature. At least a portion of the vapor stream containing hydrogen, normally gaseous hydrocarbons, saturated halogenated organic compounds and hydrogen halide is cooled and condensed to produce a second saturated halogenated organic stream and a second vapor stream containing hydrogen, normally gaseous hydrocarbons and hydrogen halide. In a preferred embodiment of the invention, the second vapor stream is contacted with a lean aqueous stream to absorb hydrogen halide compounds and to produce another vapor stream containing hydrogen and normally gaseous hydrocarbon compounds. A rich aqueous stream containing hydrogen halide compounds is recovered and used elsewhere as desired.

One embodiment of the present invention may be characterized as a process for saturating an olefin-containing halogenated organic stream to produce saturated halogenated organic compounds which process comprises the steps of: (a) contacting the olefin-containing halogenated organic stream with a hydrogen-rich gaseous stream and a liquid recycle stream comprising a saturated halogenated organic stream; (b) contacting the resulting admixture from step (a) with a hydrogenation catalyst in a hydrogenation reaction zone at selective hydrogenation conditions; (c) cooling and condensing at least a portion of the resulting effluent from the hydrogenation reaction zone to produce a saturated halogenated organic stream and a first vapor stream comprising hydrogen, saturated halogenated organic compounds and hydrogen halide; (d) recycling at least a portion of the saturated halogenated organic stream from step (c) to provide at least a portion of the liquid recycle stream in step (a);

and (e) recovering at least a portion of the saturated halogenated organic stream.

BRIEF DESCRIPTION OF THE DRAWING

The drawing is a simplified flow diagram of a preferred embodiment of the present invention.

DETAILED DESCRIPTION OF THE INVENTION

The present invention provides an improved process for the saturation of an olefin-containing halogenated organic stream to produce saturated halogenated organic compounds while minimizing the hydrodehalogenation of the organic compounds. Olefin-containing halogenated organic streams are temperature sensitive and thermally unstable. Therefore, the temperature of the olefin-containing halogenated organic feedstock is adjusted to the desired hydrogenation reaction temperature by contacting with a hydrogen-rich gaseous stream and a liquid recycle stream containing saturated halogenated compounds.

A variety of olefin-containing halogenated organic compounds are candidates for feed streams in accordance with the process of the present invention. Examples of feed streams include organic compounds containing from 2 to about 24 carbon atoms. The olefin-containing halogenated organic compounds which are contemplated as feedstocks in the present invention may contain a halogen selected from the group consisting of chlorine, bromine, fluorine and iodine. Preferred halogen compounds contain a halogen selected from the group consisting of chlorine, fluorine and bromine. A preferred olefin-containing halogenated organic feed stream is selected from the group consisting of vinyl chloride monomer production by-products and allyl chloride production by-products.

In accordance with the present invention, a feedstock containing halogenated organic compounds is introduced in admixture with hydrogen and a liquid recycle stream containing saturated halogenated organic compounds into a catalytic hydrogenation zone containing hydrogenation catalyst and maintained at selected hydrogenation conditions which favor the saturation of the olefinic bonds with hydrogen while minimizing the hydrodehalogenation of the halogenated organic compounds. This catalytic hydrogenation zone may contain a fixed, ebullated or fluidized catalyst bed. The catalytic hydrogenation zone is preferably maintained under an imposed pressure from about atmospheric to about 2000 psig and more preferably under a pressure from about 100 psig to about 1800 psig. Suitably, such reaction is conducted with a maximum catalyst bed temperature in the range of about 10° F. (−12° C.) to about 300° F. (149° C.) selected to saturate the olefinic bonds in the olefinic organic compounds. Once a suitable feedstock has been selected, a person skilled in the art will readily be able to select appropriate operating conditions to achieve the desired results based on the teachings herein. Further preferred operating conditions include liquid hourly space velocities in the range from about 0.05 $hr^{-1}$ to about 20 $hr^{-1}$ and hydrogen to feed ratios from about 20 standard cubic feet per barrel (SCFB) to about 150.000 SCFB. preferably from about 20 SCFB to about 50.000 SCFB. The recycle of saturated halogenated organic compounds to the hydrogenation reaction zone is preferably maintained in the range from about 1:1 to about 50:1 on a fresh feed volume basis.

In accordance with the present invention, the resulting effluent containing saturated halogenated organic compounds from the catalytic hydrogenation zone is cooled and introduced into a first vapor-liquid separator to produce a vapor stream containing hydrogen, saturated halogenated organic compounds and hydrogen halide and a liquid stream comprising saturated halogenated organic compounds. At least a portion of the liquid stream comprising saturated halogenated organic compounds is used for a recycle stream to attain the desired reaction zone temperature and to dilute the fresh feedstock. The remaining portion is a net product from the process.

This first vapor-liquid separator is preferably operated at a pressure from about 100 psig to about 1800 psig and a temperature from about 10° F. (−12° C.) to about 300° F. (149° C.). The resulting vapor stream containing hydrogen, saturated halogenated organic compounds and hydrogen halide is cooled, partially condensed and introduced into a second vapor-liquid separator to produce another net product stream comprising saturated halogenated organic compounds and a vapor stream containing hydrogen and hydrogen halide. This second vapor-liquid separator is preferably operated at a pressure from about atmospheric to about 1750 psig (12066 kPa gauge) and a temperature from about −40° F. (−40° C.) to about 104° F. (40° C.). This vapor stream may also contain normally gaseous hydrocarbon compounds and is, in one preferred embodiment of the present invention, contacted with a lean aqueous solution in an absorption zone to produce a hydrogen halide rich aqueous stream and vapor comprising hydrogen and possibly normally gaseous hydrocarbon compounds. The resulting hydrogen halide rich aqueous stream containing hydrogen halide compounds is removed from the absorption zone and recovered. A vapor stream containing hydrogen and possibly normally gaseous hydrocarbon compounds is removed from the absorption zone and recovered. The absorption zone is preferably maintained under a pressure which is less than the pressure of the upstream catalytic hydrogenation zone in the range from about atmospheric to about 50 psig (345 kPa gauge) and at a temperature in the range from about 40° F. (4° C.) to about 100° F. (38° C.). The wetted internals of the absorption zone are preferably constructed from carbon-based materials or organic polymers and other similar materials which are highly resistant to the corrosive effects of hydrogen halide compounds in an aqueous environment. Preferred hydrogen halide compounds are selected from the group consisting of hydrogen chloride, hydrogen fluoride and hydrogen bromide.

The preferred catalytic composite disposed within the hereinabove-described hydrogenation zone can be characterized as containing a metallic component having hydrogenation activity, which component is combined with suitable refractor carrier material of either synthetic or natural origin. The precise composition and method of manufacturing the carrier material is not considered essential to the present invention. Preferred carrier materials are alumina, silica, carbon and mixtures hereof. Suitable metallic components having hydrogenation activity are those selected from the group comprising the metals of Groups VIB and VIII of the Periodic Table, as set forth in the *Periodic Table of Elements*, E. H. Sargent and Company, 1964. Thus, the catalytic composite may comprise one or more metallic components from the group of molybdenum, tungsten, chromium, iron, cobalt, nickel, platinum, palladium, iridium, osmium, rhodium, ruthenium and mixtures thereof. The concentration of the catalytically-active metallic component, or components, is primarily dependent upon a particular metal as well as the physical and/or chemical characteristics of the particular hydrocarbon feedstock. For example, the metallic components of Group VIB are generally present in an amount within the range from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. It is further contemplated that hydrogenation catalytic composites may comprise one or more of the following components: cesium, francium, lithium, potassium, rubidium, sodium, copper, gold, silver, cadmium, mercury and zinc. Preferred hydrogenation catalysts comprise alumina and palladium.

In the drawing, the process of the present invention is illustrated by means of a simplified flow diagram in which such details as total number of reaction zones and dryer vessels, pumps, instrumentation, heat exchange and heat-recovery circuits, compressors and similar hardware have been deleted as being non-essential to an understanding of the techniques involved. The use of such miscellaneous equipment is well within the purview of one skilled in the art.

DETAILED DESCRIPTION OF THE DRAWING

With reference now to the drawing, an olefin-containing halogenated organic feed stream is introduced into the process via conduit 1 and admixed with a stream containing hydrogen and a saturated halogenated organic recycle stream supplied via conduit 12 and the resulting admixture is transported via conduit 2 and introduced into hydrogenation reaction zone 3. The resulting hydrogenated halogenated organic stream is removed from hydrogenation reaction zone 3 via conduit 4, cooled in heat-exchanger 5, transported via conduit 6 and introduced into vapor-liquid separator 7. A saturated halogenated organic stream is removed from vapor-liquid separator 7 via conduit 8 and at least a portion is removed from the process via conduit 13 and conduit 22 and recovered. Another portion of the saturated halogenated organic stream which is removed from vapor-liquid separator 7 via conduit 8 is recycled to hydrogenation reaction zone 3 via conduits 9 and 12 and heat-exchanger 28. A hydrogen stream is introduced into the process via conduit 10, heated in heat-exchanger 5 and transported via conduit 11 and conduit 12 to join the olefin-containing halogenated organic feed stream as described hereinabove. Another saturated halogenated organic stream along with a gaseous stream containing hydrogen, hydrogen halide and normally gaseous hydrocarbonaceous compounds is removed from vapor-liquid separator 7 via conduit 14, is cooled in heat-exchanger 15 and transported via conduit 16 into heat-exchanger 17. The resulting cooled stream is removed from heat-exchanger 17 via conduit 18 and introduced into vapor-liquid separator 19. A gaseous stream containing hydrogen, hydrogen halide and normally gaseous hydrocarbonaceous compounds is removed from vapor-liquid separator 19 via conduit 23 and is introduced into gas scrubber 24. An aqueous stream is introduced via conduit 26 into gas scrubber 24 and countercurrently scrubs an upwardly flowing gaseous stream to remove hydrogen halide compounds. A scrubbed gaseous stream containing hydrogen and normally gaseous hydrocarbons is removed from gas scrubber 24 via conduit 25 and recovered. An aqueous stream rich in hydrogen halide compounds is removed from gas scrubber 24 via conduit 27 and recovered. A saturated halogenated organic stream is removed from vapor-liquid separator 19 via conduit 20, heated in heat-exchanger 15 and transported via conduits 21 and 22 and removed from the process and recovered.

The following illustrative embodiment is presented for the purpose of further illustrating the process of the present invention and to indicate the benefits afforded by the utilization thereof in producing saturated halogenated organic compounds.

ILLUSTRATIVE EMBODIMENT

An olefin-containing halogenated organic feed stream having the characteristics presented in Table 1 is contacted with a heated stream containing hydrogen and recycled saturated halogenated organic compounds. The feed stream is a by-product from an allyl chloride production plant. The resulting admixture is charged to a hydrogenation reaction zone containing a palladium on alumina catalyst which is operated at selective hydrogenation conditions which include a pressure of 750 psig (5171 kPa gauge), and an average temperature of 104° F. (40° C.). The recycle of saturated halogenated organic compounds to the hydrogenation reaction zone was 20:1 on a fresh feed volume basis. The hydrogen is introduced into the hydrogenation reaction zone to at least satisfy the stoichiometric amount required to saturate the olefin-containing halogenated organic compounds.

The resulting effluent from the hydrogenation zone is cooled to a temperature of 86° F. (30° C.) and introduced to a vapor liquid separator. A portion of the liquid recovered from the vapor liquid separator is used to supply the recycle of saturated halogenated organic compounds. The net liquid effluent from the vapor liquid separator is recovered as a portion of the product of the process. A gaseous portion of the resulting effluent from the vapor liquid separator is further cooled to a temperature of about 40° F. (4° C.) and routed to a second vapor liquid separator to produce a liquid product stream and a vapor stream containing hydrogen, normally gaseous hydrocarbons and hydrogen halide. The vapor stream is contacted with water to produce an aqueous solution of hydrogen halide and a vapor stream containing hydrogen and normally gaseous hydrocarbons. The liquid recovered from the second vapor-liquid separator is recovered as another portion of the product of the process.

The total net hydrogenation zone effluent is presented in Table 2.

TABLE 1

| FEEDSTOCK COMPOSITION | |
| --- | --- |
| Propane, wt. % | 4.1 |
| Monochloropropenes, wt. % | 15.9 |
| Monochloropropanes, wt. % | 14.4 |
| Dichloropropenes | 18.8 |
| Dichloropropanes, wt. % | 46.0 |
| Benzene | 0.8 |
| TOTAL | 100.0 |
| Total Olefins, wt. % | 38.8 |

TABLE 2

| TOTAL NET PRODUCT YIELDS (FRESH FEED BASIS) | |
| --- | --- |
| Component | Weight Percent |
| Hydrogen Chloride | 8.0 |
| Propene | <0.02 |
| Propane | 8.4 |
| Chloropropenes | <0.02 |
| Chloropropanes | 33.2 |

TABLE 2-continued

TOTAL NET PRODUCT YIELDS (FRESH FEED BASIS)

| Component | Weight Percent |
|---|---|
| Dichloropropenes | <0.1 |
| Dichloropropanes | 51.0 |
| Cyclohexane | 0.7 |
| TOTAL | 101.4 |
| Chemical H$_2$ Consumption | 1.4 |

The foregoing description, Illustrative Embodiment and drawing clearly illustrate the advantages encompassed by the process of the present invention and the benefits to be afforded with the use thereof.

What is claimed:

1. A process for saturating an olefin-containing halogenated organic stream to produce saturated halogenated organic compounds which process comprises the steps of:
   (a) contacting said olefin-containing halogenated organic stream with a hydrogen-rich gaseous stream and a liquid recycle stream comprising a saturated halogenated organic stream;
   (b) contacting the resulting admixture from step (a) with a hydrogenation catalyst in a hydrogenation reaction zone at selective hydrogenation conditions;
   (c) cooling and condensing at least a portion of the resulting effluent from said hydrogenation reaction zone to produce a saturated halogenated organic stream and a vapor stream comprising hydrogen, saturated halogenated organic compounds and hydrogen halide;
   (d) recycling at least a portion of said saturated halogenated organic stream from step (c) to provide at least a portion of said liquid recycle stream in step (a); and
   (e) recovering at least a portion of said saturated halogenated organic stream.

2. The process of claim 1 wherein said hydrogenation reaction zone is operated at conditions which include a pressure from about atmospheric to about 2000 psig (13790 kPa gauge), a maximum catalyst temperature from about 10° F. (−12° C.) to about 300° F. (149° C.) and a hydrogen to feed ratio from about 20 standard cubic feet per barrel (SCFB) to about 150,000 SCFB.

3. The process of claim 1 wherein said olefin-containing halogenated organic compounds contain a halogen selected from the group consisting of chlorine, fluorine and bromine.

4. The process of claim 1 wherein said hydrogen halide is selected from the group consisting of hydrogen chloride, hydrogen fluoride and hydrogen bromide.

5. The process of claim 1 wherein said hydrogenation reaction zone contains a hydrogenation catalyst comprising palladium.

6. The process of claim 1 wherein said hydrogenation reaction zone contains a hydrogenation catalyst comprising alumina and palladium.

7. The process of claim 1 wherein said olefin-containing halogenated organic stream is selected from the group consisting of vinyl chloride monomer production by-products and allyl chloride production by-products.

8. The process of claim 1 wherein said liquid recycle stream comprising a saturated halogenated organic stream is maintained in the range from about 1:1 to about 50:1 on a fresh feed volume basis.

* * * * *